US006403631B1

(12) United States Patent
Sharp et al.

(10) Patent No.: US 6,403,631 B1
(45) Date of Patent: *Jun. 11, 2002

(54) METHOD AND COMPOSITIONS FOR ENHANCING PREGNANCY SUCCESS IN AN ANIMAL

(75) Inventors: Dan Sharp; Brian D. Cleaver, both of Gainesville, FL (US)

(73) Assignee: Equitech Laboratories, Inc., Alachua, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/483,432

(22) Filed: Jan. 14, 2000

Related U.S. Application Data

(63) Continuation of application No. 08/755,504, filed on Nov. 22, 1996, now abandoned, which is a continuation-in-part of application No. 08/563,431, filed on Nov. 24, 1995, now Pat. No. 5,792,785.

(51) Int. Cl.$^7$ ............................................ A61K 31/405
(52) U.S. Cl. ....................................... 514/415
(58) Field of Search ........................................ 514/415

(56) References Cited

U.S. PATENT DOCUMENTS

| 4,855,305 A | 8/1989 | Cohen |
| 4,882,137 A | 11/1989 | Staples et al. |
| 5,196,435 A | 3/1993 | Clemens et al. |
| 5,272,141 A | 12/1993 | Fraschini et al. |
| 5,792,785 A | 8/1998 | Sharp et al. |

FOREIGN PATENT DOCUMENTS

| EP | 0246910 | 11/1987 |
| EP | 0300630 | 1/1989 |

OTHER PUBLICATIONS

Wallace, J.M. et al. (1988) "Effect of melatonin on the peripheral concentrations of LH and progresterone after oestrus, and on conception rate in ewes" *J. Endocr.* 119:523–530.

Webley, G.E., J.P. Hearn (1987) "Local production of progesterone by the corpus luteum of the marmoset monkey in response to perfusion with chorionic gonadotrophin and melatonin in vivo" *J. Endocr.* 112:449–457.

Webley, G.E., M.R. Luck (1986) "Melatonin directly stimulates the secretion of progesterone by human and bovine granulosa cells in vitro" *J. Reprod. Fert.* 78:711–717.

Robinson, J.J., S. Wigzell, R.P. Aitken, J.M. Wallace, S. Ireland, I.S. Robertson (1991) "The modifying effects of melatonin, ram exposure and plane of nutrition on the onset of ovarian activity, ovulation rate and the endocrine status of ewes" *Animal Reproduction Science* 26:73–91.

Hearn, J.P., G.E. Webley (1987) "Regulaton of the corpus luteum of early pregnancy in the marmoset monkey: local interactions of luteotrophic and luteolytic hormones in vivo and their effects on the secretion of progesterone" *J. Endocrin.* 114:231–239.

Haresign, W., A.R. Peters, L.D. Staples (1990) "The effect of melatonin implants on breeding activity and litter size in commercial sheep flocks in the UK" *Anim. Prod.* 50:111–121.

Mori, Y., K. Shimizu, K. Hoshino (1990) "Melatonin but not the ram–effect reactivates quiescent ovarian activity of mid–anestrous ewe" *Jpn. J. Vet Sci.* 52(4):773–779.

Rekik, M. (1989) "The effect of rams and pre–treatment with progesterone or melatonin upon gonadotrophin secretion, follicular development and reproductive performance of anoestrous adult ewes" *Diss. Abst. Int. B* 49(12):5287–5288 (abstract).

Sandyk, R., P.G. Anastasiadis, P.A. Anninos, N. Tsagas (1992) "The pineal gland and spontaneous abortions: implications for therapy with melatonin and magnetic field" *Intern. J. Neuroscience* 62(3–4):243–250, MEDLINE abstract, AN 93293407.

MacPhee, A.A., P.E. Cole, B.F. Rice (1975) "The effect of melation on steroidogenesis by the human ovary in vitro" *J. Clin. Endocrinol. Metab.* 40:688–696.

Leyva, H., T. Madley, G.H. Stabenfeldt (1989) "Effect of melation on photoperiod responses, ovarian secretion of oestrogen, and coital responses in the domestic cat" *J. Reprod. Fert. Suppl.* 39:135–142.

Crosby, T.F., D. O'Callaghan (1991) "Effect of rumen degradable bolus containing melatonin or progestagen pessary plus pregnant mare serum gonadotropin on estrus response and lambing rate in ewes" *Theriogenology* 35(4):747–752.

Belibaski, S., D. Zygoyiannis, P. Davies, J.M. Doney (1993) "Milk progesterone profiles during anoestrus through to pregnancy in Greek dairy goats (*Capra prisca*): the effect of melatonin treatment and male introduction" *Anim. Prod.* 56:333–339.

Chemineau, P., E. Normant, J.P. Ravault, J. Thimonier (1987) "Induction nd persistence of pituitary and ovarian activity in the out–of–season lactating dairy goat after a treatment containing a skeleton photoperiod, melatonin and the male effect" *Chem. Abstr.* 106(3):13389.

*Primary Examiner*—Minna Moezie
*Assistant Examiner*—Mojdeh Bahar
(74) *Attorney, Agent, or Firm*—Saliwanchik, Lloyd & Saliwanchik

(57) ABSTRACT

Enhancement of pregnancy success in an animal is achieved by a method of treatment which includes administration of a single dose of melatonin during follicular development. An additional dose of melatonin can be administered during pregnancy to modulate accessory follicle formation. Novel compositions, which include a mixture of melatonin isomers or analogs, are also useful for enhancing pregnancy success.

18 Claims, 4 Drawing Sheets

METHOD AND COMPOSITIONS FOR ENHANCING PREGNANCY SUCCESS IN AN ANIMAL

CROSS-REFERENCE TO A RELATED APPLICATION

This application is a continuation of application U.S. Ser. No. 08/755,504, filed Nov. 22, 1996, now abandoned which is a continuation-in-part of application Ser. No. 08/563,431, filed Nov. 24,1995, now U.S. Pat. No. 5,792,785.

The subject invention was made with government support under a research project supported by USDA Competitive Grants Program (NRICGP) Grant Nos. 9202808 and 9001872. The government has certain rights in this invention.

FIELD OF THE INVENTION

The subject invention concerns a novel use for melatonin to regulate the uterine environment in an animal for enhanced pregnancy success.

BACKGROUND OF THE INVENTION

Melatonin has been administered in the past to treat a variety of ailments and is currently in common use in humans for regulation of biorhythms, including light-dark cycle regulation in treating depression and for treating disrupted sleep patterns, or "jet-lag," which can result from long-distance travel across time zones. Melatonin, or a derivative thereof, has also been described as being useful as a treatment for breast or other cancers.

It has been recognized that progesterone levels increase following administration of melatonin to certain animals, including sheep and marmosets. For example, Wallace et al. ([1988] *J Endocr.* 119:5–523–530) stated that melatonin orally administered to ewes increased plasma progesterone concentrations. However, the conclusion as to the effect of melatonin on the corpus luteum and improvements in conception rates were "equivocal." See Wallace et al., supra, at 529, col. 2. This reference also reveals that a 1987 paper by Webley and Hearn (*J Endocrin.* 112:449–457) reported that in vivo perfusion of melatonin to marmosets stimulated progesterone production by the marmoset corpus luteum. A 1986 Webley and Luck paper ([1986] *J Reprod. Fert.* 78:711–717) described in vitro melatonin-enhanced production of progesterone in human and bovine granulosa cells. This is in direct contrast to the results found for in vitro administration of melatonin to corpora lutea tissue according to the subject invention.

Melatonin has further been administered subcutaneously to sheep to alter the timing of the breeding season, and increased progesterone concentrations were observed. However, these studies utilized multiple, daily administrations of melatonin. Also, the aim of these treatments was not to induce increased progesterone, but to initiate reproductive cyclicity.

U.S. Pat. Nos. 5,272,141; 5,196,435; and 4,855,305 describe the use of melatonin as a contraceptive.

The subject invention, which can be distinguished from the teachings of the above references, relates to a different method of administering melatonin to effect enhanced pregnancy success. In particular, we have discovered that a single intravenous administration of melatonin to a female animal, and more particularly to a female of the Family Equidae, can provide for an improved uterine environment and corpus luteum which can enhance pregnancy success, contrary to the contraceptive use or cyclicity regulation described by certain of the prior references.

To our knowledge, use of melatonin according to the subject invention to enhance uterine environment, corpora lutea, or pregnancy success in an animal has not heretofore been described. Breeding of valuable animals, e.g., in the multimillion dollar horse-breeding industry, would derive substantial benefit from predictive and highly successful conception and pregnancy manipulation techniques. The only competing technology currently available in the horse-breeding industry is administration of progesterone exogenously, a technique that requires frequent (daily or bi-daily) and expensive ($1.00 to $3.00 daily) application for periods of up to 100 days. Multiple exogenous administrations of progesterone can maintain high circulating levels of progesterone to the extent that, if a pregnancy is misdiagnosed or is not maintained and progesterone administration is therefore withdrawn, the next normal estrous cycle is interrupted, disadvantageously preventing onset of "heat" or ovulation. A single administration of melatonin during proestrus or estrus allows for normal cycling to continue if pregnancy does not occur or if pregnancy is not maintained.

BRIEF SUMMARY OF THE INVENTION

The subject matter of this invention pertains to a single administration of melatonin to an animal during the follicular phase (proestrus or estrus) of the estrous cycle. In particular, the subject method is advantageously used to enhance pregnancy success in mammals, including a human or other mammal in which a successful pregnancy is beneficial. The subject invention can be particularly advantageous when administered to breeding livestock, e.g., an animal in the Family Equidae, which includes horses, ponies, burros, asses, zebras, and the like, or the Family Ovidae, which includes sheep. Administration of melatonin at this time during the female cycle can result in the formation of an improved endocrine or uterine environment or corpus luteum, which unexpectedly maintains production of progesterone for a period of time which can enhance pregnancy success. In addition, melatonin administration according to the subject invention can improve the metabolism, e.g., increase estrogen production, by the conceptus membrane. Our data show that administration of melatonin within a specific time frame in the female cycle can alter the morphology of the corpus luteum, which likely occurs by altering the nuclear structure or function in the corpus luteum cell. The ultimate effect of an enhanced uterine environment in the establishment and maintenance of pregnancy can enhance the growth or viability of the conceptus.

More specifically, the subject technique utilizes administration of the indole-alkylamine melatonin (N-acetyl-5-methoxytryptamine) to enhance corpus luteum steroidogenesis. Advantageously, a single, intravenous administration of melatonin during the follicular phase (proestrus or estrus) can result in formation of a corpus luteum that is considerably enhanced, e.g., increases its production of progesterone. In one embodiment of the invention, melatonin administered to a mare or ewe during the follicular phase of the cycle can increase progesterone concentrations to stimulate uterine endometrial glandular secretion, thus enhancing the uterine environment for establishment or maintenance of pregnancy and the functional development of an embryo.

Currently, a very large percentage of horse breeders administer progesterone, itself, either as an intramuscular injection or through an orally active product. Administration of these products must be done daily, or at least every other day, for a period of up to about 100 days. Typically, the cost for such progesterone treatments is approximately $1.00 or $3.00 per day per animal. In addition, such treatments are usually initiated after pregnancy can be diagnosed by standard techniques, e.g., at day 18–20 of pregnancy. Early embryonic losses between conception and about day 20 of pregnancy can be as high as 25%. In view of the discoveries relating to the subject invention, such early embryonic losses may reflect progesterone concentrations which are inadequate to prepare optimal intra-uterine conditions. However, no effective method had heretofore been described which successfully achieves the desired intra-uterine conditions, or the improved corpus luteum or conceptus membrane. A single administration to an animal of an effective dose of melatonin, appropriately timed, can provide peripherally circulating progesterone concentrations approximately equal to or in excess of those generated with daily or every-other-day administration of progesterone. Compared to the multiple administrations of progesterone commonly used in the art, a single administration of melatonin not only can stimulate a corpus luteum to increase its function, e.g., production of progesterone, but also allows for the normal regression or demise of a corpus luteum if pregnancy does not occur or is not maintained, thereby allowing the normal estrous cycle to continue.

In another embodiment of the subject invention, melatonin is administered to an animal between about day 35–45, typically at about day 40, of pregnancy for enhancing secondary corpora lutea. The administration of melatonin at approximately day 40 of pregnancy can be given as a first treatment, i.e., to a pregnant animal not previously administered melatonin at proestrus or estrus immediately prior to conception. Alternatively, the administration of melatonin can be given as a second treatment to a pregnant animal initially administered melatonin at estrus or proestrus in accordance with the subject invention. Additional administrations of melatonin according to the subject invention can also be given during pregnancy in order to effect increased progesterone levels when desired. For example, in order to calm an active or hyperactive uterus during pregnancy to prevent spontaneous abortion, melatonin in the described dose can be administered to the animal during the first or second trimester of pregnancy, typically between day 40 and day 150 of pregnancy, and more preferably, between day 50 and day 120.

In yet another embodiment of the subject invention, melatonin can be administered as a method for reducing diestrus ovulations, thereby modifying behavior of an animal, e.g., producing a calming effect in performance animals that may be less controllable than normal during diestrus ovulations.

BRIEF DESCRIPTION OF THE DRAWINGS

FIG. 5A illustrates the lack of effect in cows.

FIG. 5B shows the increased P4 concentration in ewes following administration of melatonin in accordance with the subject invention.

Figure 1A:
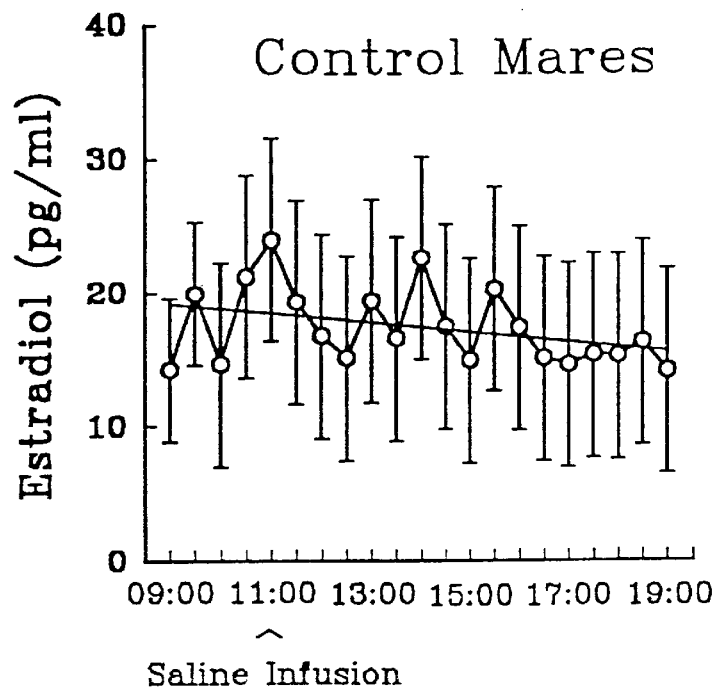
FIG. 1A shows circulating estradiol after injection (^) of control vehicle (saline).

Legend:
● -melatonin (Progest-stim™)
○ -control

DETAILED DISCLOSURE OF THE INVENTION

Enhancement of corpus luteum function and pregnancy success results from acute administration of melatonin to an animal during follicular development, e.g., in proestrus or estrus, prior to ovulation of the dominant follicle. For the purpose of this description, "follicular development" means development of the ovulatory follicle up to ovulation and includes the stage of follicle selection from the inactive pool when a developing follicle can be as small as 15 mm in size in a mare, or a comparable size in other animals. "Proestrus" is described as the period of time between regression of an existing corpus luteum and onset of estrous behavior. Regression of the existing corpus luteum occurs naturally in the event that conception does not occur. Alternatively, corpus luteum regression can be induced by treatment with a commercially available luteolysin, prostaglandin F2α (PGF; 5 mg). "Estrus" is defined as the time of sexual receptivity of a female, e.g., a mare, to a male, e.g., a stallion, and the presence of an ovarian follicle equal to or greater than 30 mm in diameter in a mare, or a comparable size in other animals. "Diestrus" is defined as the stage of the estrous cycle following ovulation and prior to the regression of the corpus luteum. A "cycling mare" refers to a mare which is ovarian and uterine intact and which is undergoing normal estrous cycle.

According to the subject invention, melatonin can be administered intravenously as a bolus, either at proestrus (e.g., day 2 after PGF administration) or estrus (minimum 3 days behavioral estrus plus a follicle, in mares, of ≧30 mm diameter). In one embodiment of the invention, melatonin, which is commercially available, can be administered at a dose of less than 3 μg per pound of body weight, typically about 0.2 μg per pound of body weight of a mare, and preferably up to about 2.0 μg per pound of body weight in a ewe. For example, a 500-lb pony mare can be treated according to the subject invention by administering melatonin at a dose of about 100 μg, typically at a concentration of about 100 μg in 1 ml of sterile physiological saline. The dosage, however, can be variable and adjusted according to several factors, including the species of animal being treated.

In accordance with the subject invention, melatonin can be administered at a dosage as low as 0.01 μg per pound of body weight, and as high as 3 μg per pound of body weight to produce the desired effects. A preferred dose in mares is between about 0.1 μg per pound of body weight and about 0.5 μg per pound of body weight. A preferred dose in ewes is about 1.0 μg per pound of body weight to about 2.0 μg per pound of body weight.

In addition, it is understood in the art that melatonin is available in various derivative, isomeric, or analog forms. These derivative, isomeric, or analog forms include halogenated analogs of natural melatonin, preferably analogs which are halogenated at the 2-position, e.g., 2-iodomelatonin, 2-bromo-melatonin, and the like. Other substitutions to the 2-position on the natural melatonin molecule can also be used. For example, organic substituted melatonins are also known in the art. Organic-substituted melatonin includes hydrocarbon chains of 1–4 carbons in length, also preferably at the 2-position of melatonin. A sulfur- or nitrogen-containing molecule can also be substituted on the melatonin molecule to produce an effective derivative or analog.

The subject invention can include the use of melatonin, an analog or isomer of melatonin, or a combination thereof. In addition, congeners or derivatives of melatonin or isomers or analogs of those congeners or derivatives can also be employed in the method of the subject invention. These variations of melatonin can be used according to the subject invention so long as the analogs, congeners, derivatives, or isomers retain biological activity substantially the same as natural melatonin. For example, an analog, congener, derivative, or isomer of melatonin, having binding capability to a natural melatonin receptor similar to the binding capability of natural melatonin, would be considered to sufficiently retain biological activity in accordance with the subject invention.

Figure 1B:
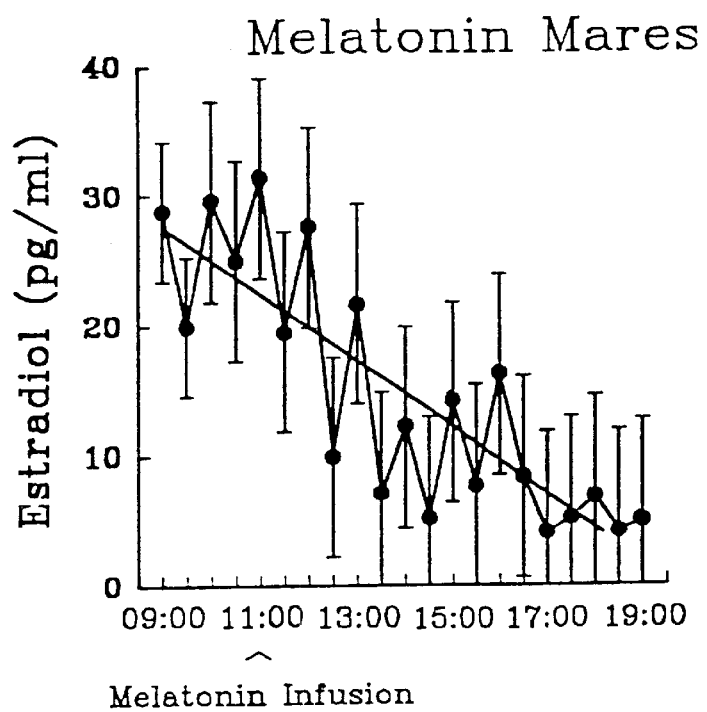
FIG. 1B shows circulating estradiol concentrations following a bolus injection (^) of 100 μg of melatonin.
Figure 2:
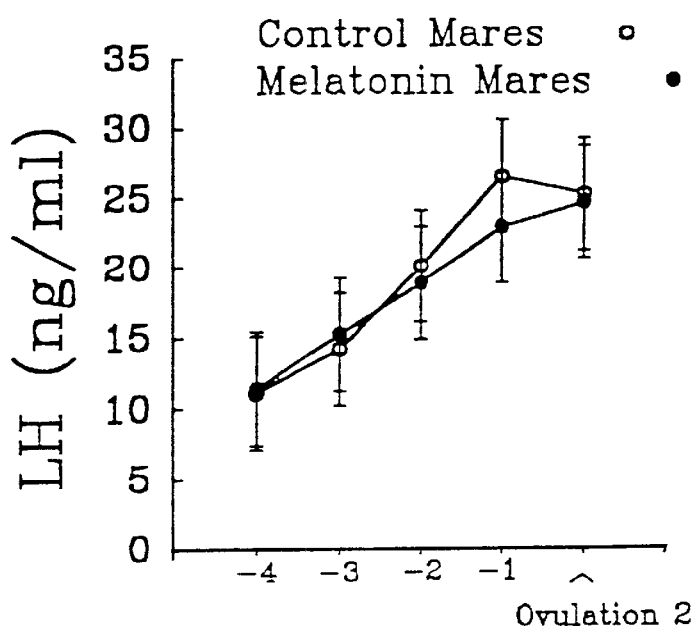
FIG. 2 shows the effect of melatonin on circulating luteinizing hormone (LH).
Figure 3:
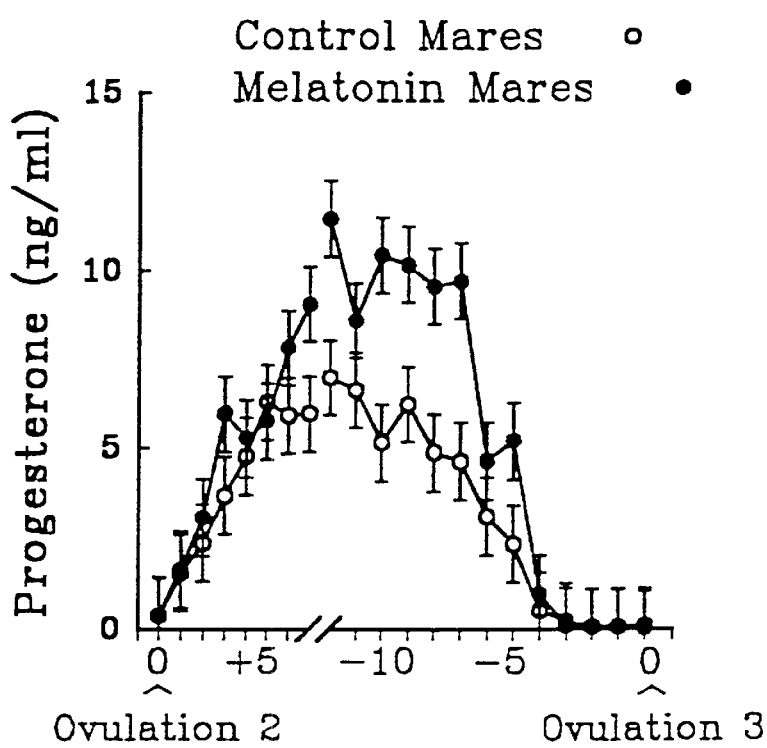
FIG. 3 shows the effect of a single, acute infusion of melatonin on progesterone production throughout the entire luteal phase of the cycle.

The immediate effect of acute melatonin administration is an unexpected decrease in circulating estradiol concentrations (see FIGS. 1a and 1b). Also unexpectedly, there is no effect on luteinizing hormone (LH) secretion (see FIG. 2). However, there is a highly significant increase in secretion of progesterone throughout the entire subsequent luteal phase (see FIG. 3). Melatonin administration prior to formation of the corpus luteum, during the development of the ovulatory follicle (follicular development), can advantageously lead to changes in corpus luteum function (morphological or biochemical) that persist throughout the life span of the corpus luteum. Thus, a single administration of melatonin given to an animal, prior to breeding or conception, i.e., in the follicular development phase of its cycle, can lead to prolonged elevation of circulating progesterone concentrations to produce an advantageous uterine environment or pregnancy success. Pregnancy success can include maintenance of a pregnancy that otherwise may have failed, or can include the production of a larger or more viable conceptus or neonate. Melatonin administered in accordance with the subject invention was shown to result in significantly larger embryos (see FIG. 4). Accessory follicles can also benefit from melatonin administration at a time prior to the normal decrease in progesterone levels during the cycle, i.e., prior to ovulation or luteinization of the accessory follicles. The need for expensive, time-consuming, and labor-intensive progesterone administration can thereby be obviated.

Figure 5A:
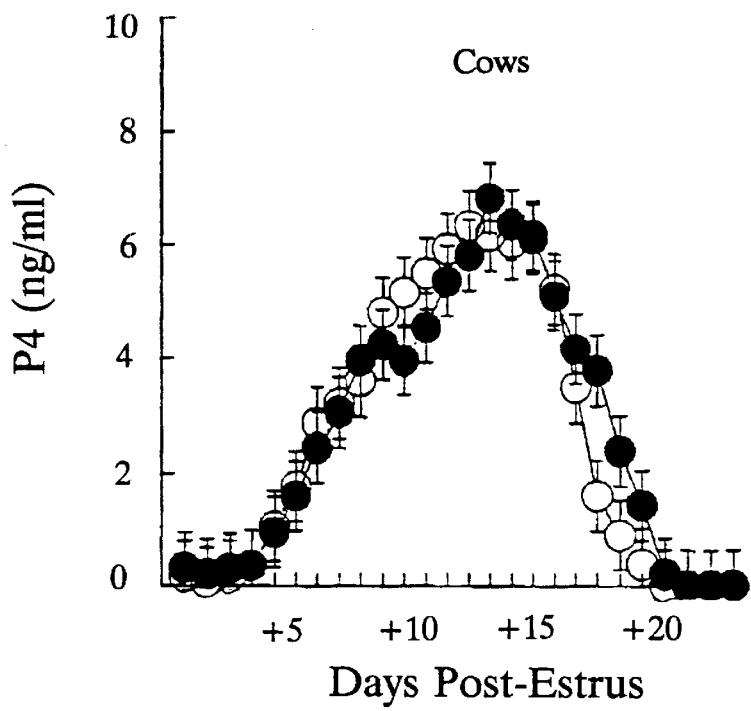
FIGS. 5A and 5B show the effect on plasma progesterone (P4) concentration (ng/ml), compared to a saline control, following administration of melatonin to cows and ewes in accordance with the subject invention.

Initial results of administering melatonin in cows showed no effect on plasma progesterone (P4) concentrations. See FIG. 5A. Administration of melatonin in accordance with the subject invention was found to increase plasma progesterone levels in ewes. See FIG. 5B.

Following are examples which illustrate procedures for practicing the invention. These examples should not be construed as limiting. All percentages are by weight and all solvent mixture proportions are by volume unless otherwise noted.

EXAMPLE 1

Bolus Administration of Melatonin on Mares in Estrus

A. Effect of bolus administration of melatonin on estradiol, progesterone, and luteinizing hormone levels. The effect of bolus melatonin administration during estrus on plasma estradiol (E2), progesterone (P4), and luteinizing hormone (LH) was determined. The interval from treatment to ovulation (OV1) and duration of the subsequent estrous cycle, ending at OV2, were also measured. Estrous cycles of eight pony mares were synchronized. Ovarian follicular activity was monitored daily, and sexual behavior was monitored with a stallion. Blood samples were collected daily. Upon detection of behavioral estrus and a 30 mm diameter follicle, mares were assigned to either a control group or melatonin group. Blood samples were collected for 8 hours (09:00 to 17:00) at 30 minute intervals. Melatonin-group mares were given an injection of 100 µg melatonin in 1 ml of sterile saline into the jugular vein, while control-group mares received 1 ml sterile saline. Tests for homogeneity of regression for plasma E2 found that secretion declined ($p<0.001$) following administration. The pattern of E2 in control-group mares was best described as cubic, with increases occurring at both OV1 and OV2, whereas the pattern of E2 in melatonin-group mares was quadratic, with increases noted only at OV2. The pattern of plasma P4 in both melatonin-group and control-group mares was significant at the quadratic level with higher ($p<0.007$) P4 levels observed in the melatonin-group mares. The interval from treatment to OV1 and duration of subsequent estrous cycles (interval from OV1 to OV2) did not differ between groups. Plasma LH levels were not different between groups. These results show that treatment with melatonin altered the patterns of circulating ovarian steroids in pony mares.

B. Effect on conception of bolus administration of melatonin during estrus. Mares were treated with either control (1.0 ml 0.9% injectable saline, n=4) or melatonin (100 µg melatonin in 1.0 ml 0.9% injectable saline, n=4) administered at estrus upon detection of at least a 30 mm diameter follicle and sexual receptivity to the stallion. Ovarian follicular activity was monitored daily by rectal palpation and/or ultrasonography. Pregnancy was monitored by ultrasonography after day 10 post-ovulation.

Blood samples were collected daily from the day of treatment to day 16 post-ovulation, when conceptuses were removed. Conceptus diameter was measured daily beginning day 10 post-ovulation with ultrasound.

Figure 4:
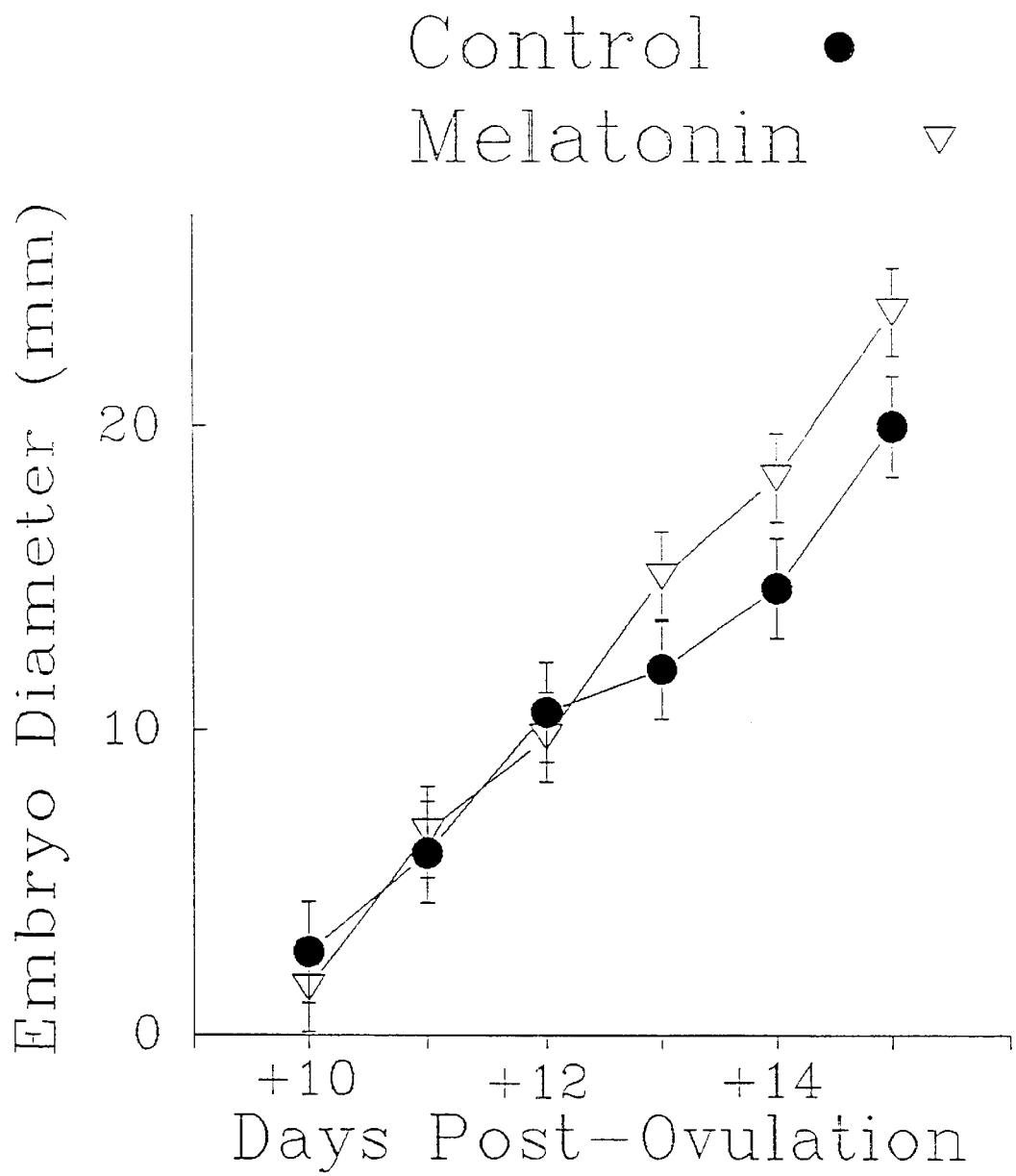
FIG. 4 shows increased diameter of embryos in animals administered melatonin according to the subject invention.

Results and conclusions. Plasma progesterone concentrations of melatonin-treated mares were different ($p=0.026$) from control mares. Orthogonal comparisons among days indicated that conceptuses removed from melatonin-treated mares were significantly larger after day 13 post-ovulation. Early embryonic growth rate did not appear to differ from days 10 to 13, but conceptus diameter was larger in melatonin-treated mares from day 13 to 15 (FIG. 4). Plasma progesterone concentrations were increased, as observed in previous experiments in cyclic mares. These data show that melatonin treatment, and the resultant increase in progesterone, can stimulate uterine secretions, which enhanced conceptus growth.

EXAMPLE 2

Administration of Melatonin at Proestrus

Acute administration of melatonin to cyclic pony mares at proestrus resulted in decreased estradiol (E2) concentrations but had no effect on plasma luteinizing hormone (LH), and progesterone concentrations were increased. Treatments were administered at 09:59:45 at proestrus only. Test animals were divided into two groups: control (1.0 ml 0.9% saline, n=3), and melatonin (100 µg melatonin in 1.0 ml 0.9% saline, n=3). Ovarian follicular activity was monitored daily by rectal palpation and/or ultrasonography. Blood samples were collected every 10 minutes for a period of 8 hours at proestrus, estrus, and diestrus. Plasma melatonin concentrations were measured by radioimmunoassay (RIA) to determine the effect of control and melatonin treatments administered at proestrus.

Results and conclusions. Administration of 100 $\mu$g melatonin resulted in plasma melatonin concentrations which were significantly (p=0.0001) higher than in control mares. Plasma melatonin concentrations decreased over the next two hours and were not different from plasma melatonin concentrations of control mares by 3 hours post-treatment. Plasma estradiol (E2) concentrations at proestrus did not change over the 8-hour sampling period in control mares; however, plasma estradiol concentrations of melatonin-treated mares decreased following treatment. Mean plasma estradiol concentrations in control and melatonin-treated mares were not different at proestrus or diestrus but were lower (p=0.006) in melatonin-treated mares at estrus. Mean plasma progesterone (P4) concentrations in control and melatonin-treated mares were not different at proestrus or estrus but were significantly higher (p=0.001) in melatonin-treated mares at diestrus. During the 8-hour proestrus sampling period, plasma LH concentrations were not different between the two treatments. These data show that treatment with melatonin at proestrus did not alter plasma LH concentrations but did result in altered concentrations of estradiol and progesterone throughout the subsequent estrous cycle.

EXAMPLE 3

Administration of Melatonin at Estrus or Proestrus

Administration of melatonin to cyclic pony mares at either proestrus or estrus resulted in increased progesterone concentrations following ovulation. The treatment schedule was as follows: treatments were administered at 10:59:45 at either proestrus or estrus to four groups of animals: proestrus control (1.0 ml 0.9% saline, n=4), proestrus melatonin (100 $\mu$g melatonin in 1.0 ml 0.9% saline, n=4), estrus control (1.0 ml 0.9% saline, n=4), and estrus melatonin (100 $\mu$g melatonin in 1.0 ml 0.9% saline, n=4). Blood samples were collected every 30 minutes and were collected daily through the next subsequent estrus and ovulation. Ovarian follicular activity was monitored daily by rectal palpation and/or ultrasonography.

Results and conclusions. Treatment with melatonin at proestrus was not different from treatment at estrus. Treatment with melatonin at estrus resulted in an acute decline in plasma estradiol concentrations. Plasma progesterone concentrations in blood samples taken daily during the subsequent estrous cycle were analyzed in two ways. The first method of analysis organized samples from the day of ovulation through the day of the next subsequent ovulation. Utilizing this method of analysis, plasma progesterone response to melatonin treatment was higher (p=0.007) in the treated group as compared to control mares. Data were also analyzed by standardizing all mares from ovulation to day 7 post-ovulation and from the next subsequent ovulation backwards. The reason for this standardization is that not all mares undergo corpus luteum regression at the same time. Thus, it is important to show time trends of progesterone increase during the immediate post-ovulation time, and to show the decline in progesterone concentrations after corpus luteum regression. When analyzed in this manner, progesterone was significantly (p=0.01) higher in melatonin-treated mares than in control mares. Estradiol concentrations were analyzed in the same manner and were also found to be different (p=0.001) compared to control mares, but plasma LH concentrations did not differ between the melatonin treatments and the controls. Therefore, treatment with melatonin at either proestrus or estrus resulted in higher progesterone concentrations during the subsequent diestrus period, an acute decline in plasma estradiol concentrations at the time of treatment, and altered estradiol concentrations during the subsequent estrous cycle. There was no significant effect on the pre-ovulatory LH increase in the initial ovulation following treatment or the next subsequent ovulation.

EXAMPLE 4

Administration of Melatonin at Diestrus

Melatonin treatments were administered at 8 days after ovulation (mid-diestrus) to mares in either a control group (1.0 ml 0.9% saline, n=4) or a melatonin group (100 $\mu$g melatonin in 1.0 ml 0.9% saline, n=4). Treatments were given at 10:59:45. Daily blood sampling was performed from estrus preceding treatment to 7 days after the next subsequent ovulation. Blood samples were collected every 30 minutes for 10 hours each day of sampling.

Results and conclusions. Administration of melatonin on day 8 post-ovulation did not alter plasma progesterone concentrations during a 10-hour sampling period. Nor were plasma progesterone concentrations different throughout the rest of the luteal phase. However, plasma progesterone concentrations following the next subsequent ovulation were significantly (p=0.034) higher until day 7 post-ovulation. These experiments showed that treatment with melatonin at mid-diestrus had no acute or chronic effect on luteal progesterone production. However, treatment with melatonin during diestrus did result in a transient increase in plasma progesterone concentrations during early diestrus of the next subsequent estrous cycle. This indicates that the follicle developing in mid-diestrus and destined to ovulate during the next subsequent estrus was affected by melatonin treatment.

EXAMPLE 5

Administration of Melatonin at Different Times of Day: AM v. PM

Administration of melatonin to hysterectomized mares at estrus results in increased plasma progesterone concentrations after ovulation. Because hysterectomized mares are unable to generate a luteolytic secretion of prostaglandin F2$\alpha$ (PGF), luteal function and progesterone production continue longer than in uterine-intact mares. The advantageous progesterone production gained by melatonin administration may be maintained in a mare with prolonged luteal function. Furthermore, the time of melatonin administration at estrus (morning versus afternoon) does not affect the plasma progesterone response.

Treatment was either control (1.0 ml 0.9% saline, n=4) or melatonin (100 $\mu$g melatonin in 1.0 ml 0.9% saline, n=4) and was administered at estrus upon detection of at least a 30 mm diameter follicle and sexual receptivity to the stallion. Ovarian follicular and luteal activity was monitored daily by rectal palpation and/or ultrasonography. The experiment was repeated in full using the same design with the exception that melatonin or control injections were administered in the afternoon rather than the morning. Blood samples were collected daily from day of treatment for 30 days post-ovulation.

Results and conclusions. Plasma progesterone concentrations were higher (p<0.03) in mares administered melatonin in the morning or afternoon compared with control mares. In both morning and afternoon treated mares, progesterone was significantly elevated in melatonin-treated mares until approximate time of luteal regression (day 14 to 16) when there were no longer detectable differences between melatonin-treated and saline-treated mares. However, after day 16 post-ovulation, plasma progesterone concentrations appeared to converge in control and melatonin-treatment groups. Comparison of plasma progesterone concentrations of morning, afternoon, or cyclic melatonin- or control-treated mares indicates that the period of decreased progesterone concentrations in hysterectomized, melatonin-treated mares corresponds to the time of normal luteal regression in control or melatonin-treated cyclic mares. These data show that hysterectomized mares respond to melatonin administration at estrus in a similar manner to cyclic mares and time-of-day of melatonin treatment does not affect enhancement of luteal progesterone production. However, circulating progesterone concentrations decrease somewhat around the time of normal luteolysis in cyclic mares, regardless of treatment.

EXAMPLE 6

Multiple Administrations of Melatonin

Mares are unique in that they develop and ovulate a new cohort of follicles around day 35–45 of pregnancy. The resulting corpora lutea are called "accessory corpora lutea." Melatonin treatment just prior to formation of the accessory corpora lutea is expected to result in enhanced progesterone production by the accessory corpora lutea.

To determine whether melatonin administration enhances progesterone production by the accessory corpora lutea, treatments of either a control (1.0 ml 0.9% saline, n=4) or a melatonin (100 $\mu$g melatonin in 1.0 ml 0.9% saline, n=4) were administered to mare at estrus upon detection of at least a 30 mm diameter follicle and sexual receptivity to the stallion. Ovarian follicular and luteal activity was monitored daily by rectal palpation and/or ultrasonography. Mares which received melatonin treatment at estrus also received daily melatonin treatment from day +35 to day +45 of pregnancy.

EXAMPLE 7

Effect of Melatonin on Conceptus Membranes
(In Vitro)

Treatment with melatonin at estrus results in greater in vitro estradiol biosynthetic capability of day 16 conceptus membrane segments given androgen precursors. To demonstrate this, conceptuses from mares were flushed transcervically on day 16 post-ovulation. The extra-embryonic membranes were dissected into 4×4 mm$^2$ segments and cultured in the presence or absence of supplemental testosterone. Conceptus membrane fragments were cultured for 24 hours and the culture medium analyzed for estradiol.

Results and conclusions. Following completion of culture, conceptus membrane segments were frozen and assayed for DNA content. All estradiol concentrations measured in culture media were then adjusted for the DNA content of the appropriate conceptus membrane segment. In the absence of supplemental testosterone in the culture media, estradiol concentrations in media of conceptus tissue from control and melatonin-treated conceptuses did not differ. Testosterone supplied to the culture significantly increased estradiol production by conceptuses in vitro, but conceptuses from melatonin-treated mares produced significantly more estradiol in the presence of testosterone than did conceptus membranes from mares treated with saline. Testosterone supplementation allowed for greater estradiol production, and conceptuses from melatonin-treated mares produced significantly (p=0.01) greater estradiol than all other groups. Thus, treatment with melatonin during estrus resulted in conceptuses with greater steroidogenic capabilities when supplied with androgen (testosterone) to act as a precursor. This shows that conceptuses from melatonin-treated mares can have increased progesterone which, in turn, results in a uterine environment which can enhance to conceptus growth and metabolic development.

EXAMPLE 8

Effect of Melatonin on Corpora Lutea Tissues
(In Vitro)

Incubation with melatonin of segments of corpora lutea from cycling mares does not alter progesterone production in vitro. Corpus luteum tissue was collected surgically and was dissected into segments approximately 2×2 mm$^2$. Segments were incubated in the following manner:

| Plate 1: | wells 1–6 | media only |
|---|---|---|
| | wells 7–12 | media + 1 nM melatonin |
| | wells 13–18 | media + 100 ng human chorionic gonadotropin (hCG) |
| | wells 19–24 | media + 1 nM melatonin + 100 ng hCG |
| Plate 2: | wells 1–6 | media only |
| | wells 7–12 | media + 10 nM melatonin |
| | wells 13–18 | media + 100 ng human chorionic gonadotropin (hCG) |
| | wells 19–24 | media + 10 nM melatonin + 100 ng hCG |
| Plate 3: | wells 1–6 | media only |
| | wells 7–12 | media + 100 nM melatonin |
| | wells 13–18 | media + 100 ng human chorionic gonadotropin (hCG) |
| | wells 19–24 | media + 100 nM melatonin + 100 ng hCG |

At completion of culture, segments were frozen until assayed for DNA content. All media progesterone concentrations were subsequently adjusted for DNA content of the appropriate segment.

Results and conclusions. Supplementation of luteal tissue in vitro with hCG resulted in significantly higher (p=0.033) media progesterone concentrations when compared with segments incubated in the absence of hCG. However, melatonin had no effect on media progesterone concentrations in the presence or absence of hCG. These results demonstrate that in vitro progesterone production by luteal tissue collected from normal, cycling mares was not altered by culture in the presence of melatonin, regardless of dose.

EXAMPLE 9

Effect on Corpora Lutea Morphology by Estrus-Administered Melatonin

Following collection of conceptuses as described in Examples 7 and 8, mares were taken to surgery and the corpus luteum biopsied. Biopsies were taken from each mare, control and melatonin-treated, for both light and electron microscopy. Mares administered melatonin at estrus resulted in the formation of a corpus luteum with a greater percent of cells with pleomorphic nuclei and/or greater luteal cell progesterone synthetic capability, which can result in the observed increase in plasma progesterone concentrations.

EXAMPLE 10

Treatment Procedure

A. Preparation of 100 ml melatonin composition. Ten (10) milligrams of crystalline melatonin (Sigma Scientific) was weighed and, under sterile conditions (autoclaved), physiological saline was added to a final volume of 100 ml to give a final concentration of 100 $\mu$melatonin/1 ml of saline. The solution was aliquoted into 1 ml injection port vials and sealed. The aliquoted composition was stored in amber bottles to minimize photic degeneration. The melatonin solution was stored at room temperature.

B. Treatment procedure for a mare. A mare is monitored for estrous behavior daily with a vigorous "teaser" stallion, and follicular development and/or incidence of ovulation is monitored every third day, or daily if a follicle greater than 30 mm diameter is detected, by transrectal palpation and transrectal ultrasound examination of the ovaries.

To assure that a mare is at a known stage of the estrous cycle, the corpus luteum can be regressed by administration of prostaglandin F2$\alpha$ (PGF; 5 mg/mare, intramuscularly). A mare can be treated during proestrus or estrus, defined as follows: proestrus is the interval from regression of the corpus luteum to onset of estrous behavior. In these experiments, treatment was administered 2 days after PGF administration. Estrus is the period of the estrous cycle when mares accept breeding by a stallion. In these experiments, estrus was defined as having estrous behavior for a minimum of 2 days, and a follicle greater than 30 mm diameter present. About 100 $\mu$g melatonin is administered intravenously by jugular venipuncture, typically using a 20-gauge needle, and 1 cc syringe.

EXAMPLE 11

Formulation and Administration

The melatonin compounds of the invention, which can include various known isomers or analogs of melatonin, are useful for various non-therapeutic and therapeutic purposes. It is apparent from the testing that the compounds of the invention are effective for increasing progesterone production by the corpus luteum and enhanced pregnancy success.

Application of the melatonin compounds and compositions containing them can be contemplated to be accomplished by any suitable therapeutic method and technique presently or prospectively known to those skilled in the art. Further, the melatonin compounds of the subject invention have use as starting materials or intermediates for the preparation of other useful compounds and compositions.

The dosage administration to a host in the above indications will be dependent upon the identity of the infection, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions comprising at least one melatonin compound of the subject invention can be formulated such that an effective amount of the bioactive compound(s) is combined with a suitable carrier in order to facilitate effective administration of the composition.

EXAMPLE 12

Bolus Administration of Melatonin on Ewes in Estrus

Figure 5B:
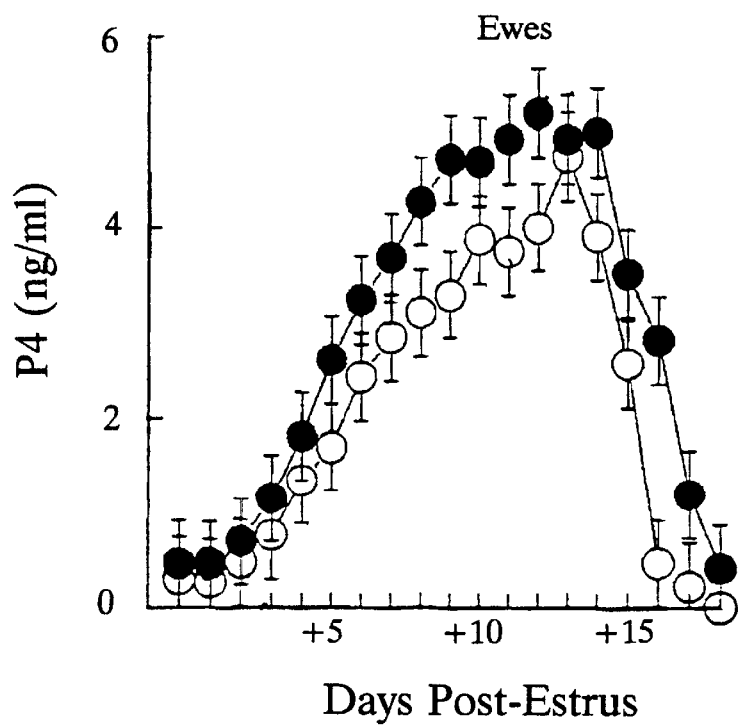

A. Effect of bolus administration of melatonin on progesterone levels. The effect of bolus melatonin administration during estrus on plasma progesterone was determined. The duration of the estrous cycle was also measured. Estrous cycles of ten ewes were monitored by daily behavioral monitoring with a vasectomized ram. The first day ewes displayed sexual receptivity was regarded as Day 0. Blood samples were collected daily for an entire estrous cycle. Melatonin-treated ewes (n=5) were administered 400 $\mu$g melatonin i.v. in the early morning (07:30 to 08:30hr) and late afternoon (16:30 to 17:30hr). Five ewes were treated similarly, but were administered saline as control at the same times. Estrus duration was approximately 24 to 36 hr, thus ewes were administered 2 to 3 doses of melatonin to assure treatment during estrus. Progesterone levels were higher from Day 5 to Day 15 post-estrus in melatonin-treated ewes compared with saline-treated ewes. The increased progesterone concentrations following administration of melatonin, as compared to a saline control, is shown in FIG. 5B.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for enhancing pregnancy success in an animal, said method comprising administering to said animal an effective amount of melatonin, or one or more analogs that exhibit melatonin biological activity, wherein said melatonin analog is substituted at the 2-position with a halogen or a hydrocarbon of 1 to 4 carbon atoms, and wherein said melatonin or analog thereof is administered only during folliculer development in the reproductive cycle of said animal.

2. The method according to claim 1, wherein said effective amount is between about 0.02 $\mu$g and about 3 $\mu$g per pound body weight of the animal.

3. The method according to claim 2, wherein said animal is a mammal.

4. The method according to claim 3, wherein said mammal is a female in the Family Equidae.

5. The method according to claim 4, wherein said effective amount is between about 0.01 $\mu$g and about 0.5 $\mu$g per pound body weight of the mammal.

6. The method according to claim 4, wherein said effective amount is about 0.2 $\mu$g per pound body weight of the mammal.

7. The method according to claim 3, wherein said mammal is a female in the Family Ovidae.

8. The method according to claim 7, wherein said effective amount is between 1.5 $\mu$g and 3.0 $\mu$g per pound of body weight of the mammal.

9. The method according to claim 8, wherein said effective amount is about 2.0 $\mu$g per pound of body weight of the mammal.

10. The method according to claim 4, wherein said Equid is selected from the group consisting of horse, pony, burro, ass, and zebra.

11. The method according to claim 4, wherein said Equid is a mare.

12. The method according to claim 1, wherein said administration during follicular development is at least prior to ovulation.

13. The method according to claim 1, wherein said administration is during estrus.

14. The method according to claim 1, wherein said melatonin analog is selected from the group consisting of 2-iodo-melatonin and 2-bromo-melatonin.

15. The method according to claim 1, wherein at least two different analogs of melatonin are administered to said animal.

16. The method according to claim 1, wherein natural melatonin is administered to said animal in conjunction with said melatonin analog.

17. The method according to claim 1, wherein said reproductive cycle is a menstrual cycle.

18. The method according to claim 1, wherein the reproductive cycle is an estrous cycle.

* * * * *